(12) United States Patent
Paulus et al.

(10) Patent No.: US 7,413,859 B2
(45) Date of Patent: Aug. 19, 2008

(54) METHOD AND BIOSENSORS FOR DETECTING MACROMOLECULAR BIOPOLYMERS

(75) Inventors: Christian Paulus, Weilheim (DE); Petra T. Schindler-Bauer, Vaterstetten (DE)

(73) Assignee: Siemens Aktiengesellschaft, DEX ( * ) Notice: Subject to any disclaimer, the term of this patent is extended or adjusted under 35 U.S.C. 154(b) by 294 days.

(21) Appl. No.: 10/841,413

(22) Filed: May 7, 2004

(65) Prior Publication Data
US 2005/0136423 A1    Jun. 23, 2005

Related U.S. Application Data

(63) Continuation of application No. PCT/DE02/04171, filed on Nov. 11, 2002.

(30) Foreign Application Priority Data
Nov. 14, 2001    (DE) ................................. 101 55 892

(51) Int. Cl.
*C21Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search .................. 435/6, 435/283.1; 536/23.1, 24.3
See application file for complete search history.

(56) References Cited

U.S. PATENT DOCUMENTS

| | | | |
|---|---|---|---|
| 5,312,527 A | | 5/1994 | Mikkelsen et al. |
| 5,648,213 A | | 7/1997 | Reddy et al. |
| 5,804,384 A | * | 9/1998 | Muller et al. ................... 435/6 |
| 5,972,692 A | | 10/1999 | Hashimoto et al. |
| 6,017,696 A | | 1/2000 | Heller |
| 6,168,948 B1 | | 1/2001 | Anderson et al. |
| 6,238,910 B1 | * | 5/2001 | Custance et al. .......... 435/287.2 |
| 6,365,731 B1 | * | 4/2002 | Brown et al. .............. 536/25.42 |
| 6,596,487 B2 | * | 7/2003 | Raees et al. ...................... 435/6 |
| 7,056,664 B1 | * | 6/2006 | Hartwich et al. ................ 435/6 |
| 7,118,860 B2 | * | 10/2006 | Sorge et al. ...................... 435/6 |
| 2002/0110808 A1 | * | 8/2002 | Reidhaar-Olson .............. 435/6 |
| 2005/0003366 A1 | * | 1/2005 | Getts ............................... 435/6 |

FOREIGN PATENT DOCUMENTS

| | | |
|---|---|---|
| DE | 199 40 810 A1 | 5/2000 |
| DE | 199 26 457 A1 | 7/2000 |
| DE | 199 16 921 A1 | 10/2000 |
| WO | WO-94/05414 A1 | 3/1994 |
| WO | WO-99/53093 A1 | 10/1999 |
| WO | WO-00/42217 A2 | 7/2000 |
| WO | WO-01/75151 A2 | 10/2001 |

OTHER PUBLICATIONS

Brown et al. Molecular beacons attached to glass beads fluoresce upon hybridization to target DNA. Chem Commun (Camb) 7 : 621-622 (2000).*
R. Hintsche et al., "Microbiosenses Using Electrodes Made in Si-technology", Frontiers in Biosensorics, Fundamental Aspects, edited by F.W. Scheller et al., Dirk Hauser Verlag, Basel, pp. 267-283, 1997.
R. Hintsche, et al., "Microelectrode arrays and applicatino to biosensing devices", Biosensors & Bioelectronics, vol. 9, pp. 697-705, 1994.
M. Paeschke, et al., "Voltammetric Multichannel Measurements Using Silicon Fabricated Microelectrode Arrays", Electroanalysis, vol. 7, Nr. 1, pp. 1-8, 1996.
P. van Gerwen, et al., "Nanoscaled Interdigitated Electrode Arrays for Biochemical Sensors", IEEE, International Conference on Solid-State Sensors and Actuators, Chicago, pp. 907-910, Jun. 16-19, 1997.
N.L. Thompson, et al., "Total Internal Reflection Fluorescence: Applications in Cellular Biophysics", Current Opinion in Biotechnology, vol. 8, pp. 58-64, 1997.
J. G. Wetmur, "DNA Probes: Applications of the Principles of Nucleic Acid Hybridization", Critical Reviews in Biochemistry and Molecular Biology, 26 (3/4) pp. 227-259, 1991.
E. Braun, et al., "DNA-templated assembly and electrode attachment of a conducting silver wire", Nature, vol. 391, pp. 775-778, 1998.
Roche Molecular Biochemicals, 1999 Biochemicals Catalog, p. 99.

* cited by examiner

*Primary Examiner*—Ethan Whisenant
(74) *Attorney, Agent, or Firm*—Dickstein, Shapiro, LLP.

(57) ABSTRACT

Method for detecting macromolecular biopolymers using a unit for immobilizing macromolecular biopolymers, in which the unit is provided with first molecules serving as capture molecules. The method includes the steps of bringing a sample into contact with the unit, it being possible for the sample to contain the macromolecular biopolymers, and the macromolecular biopolymers or the first molecules having a marking which is used to generate a detectable signal, binding macromolecular biopolymers contained in the sample to the capture molecules, thereby forming complexes comprising capture molecules and macromolecular biopolymers, exciting the emission of a signal by means of the marking, detecting the signal emitted by means of the marking, separating the complexes comprising capture molecules and macromolecular biopolymers, thereby altering the intensity of the emitted signal, and detecting the separation of the complexes comprising capture molecules and macromolecular biopolymers by means of the change in the intensity of the signal.

24 Claims, 8 Drawing Sheets

METHOD AND BIOSENSORS FOR DETECTING MACROMOLECULAR BIOPOLYMERS

CROSS-REFERENCE TO RELATED APPLICATION

This application is a continuation of International Patent Application Serial No. PCT/DE02/04171, filed Nov. 11, 2002, which published in German on Jun. 5, 2003 as WO 03/046209, and is incorporated herein by reference in its entirety.

FIELD OF THE INVENTION

The invention relates to methods for detecting macromolecular biopolymers using at least one unit for immobilizing macromolecular biopolymers and to a biosensor for detecting macromolecular biopolymers.

BACKGROUND OF THE INVENTION

R. Hintsche et al., Microbiosensors Using Electrodes Made in Si-Technology, Frontiers in Biosensorics, Fundamental Aspects, edited by F. W. Scheller et al., Dirk Hauser Verlag, Basel, pp. 267-283, 1997, R. Hintsche et al., Microelectrode arrays and application to biosensing devices, Biosensors & Bioelectronics, Vol. 9, pp. 697-705, 1994, M. Paeschke et al., Voltametric Multichannel Measurements Using Silicon Fabricated Microelectrode Arrays, Electroanalysis, Vol. 7, No. 1, pp. 1-8, 1996, and P. van Gerwen, Nanoscaled Interdigitated Electrode Arrays for Biochemical Sensors, IEEE, International Conference on Solid-State Sensors and Actuators, Chicago, pp. 907-910, Jun. 16-19, 1997, disclose methods for detecting DNA molecules in which biosensors based on electrode arrangements are used for detection.

Figure 2A:
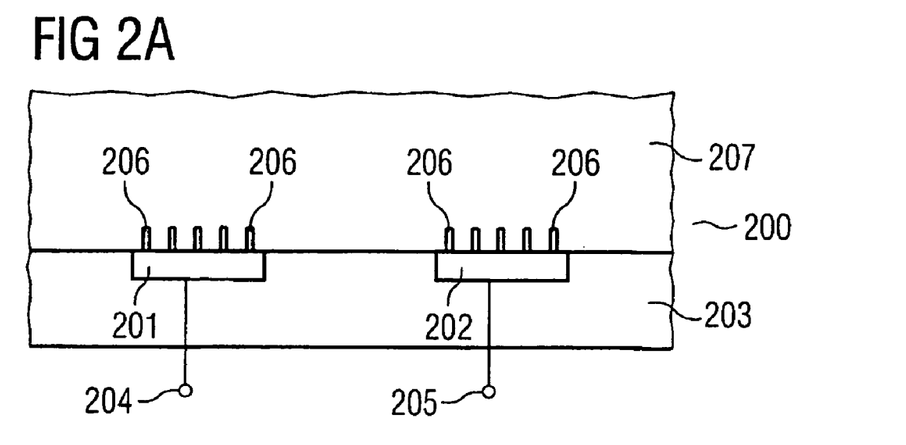
FIGS. 2a and 2b show a sketch of two planar electrodes which can be used to detect the existence of DNA strands to be detected in an electrolyte (FIG. 2a) or the nonexistence thereof (FIG. 2b)
Figure 2B:
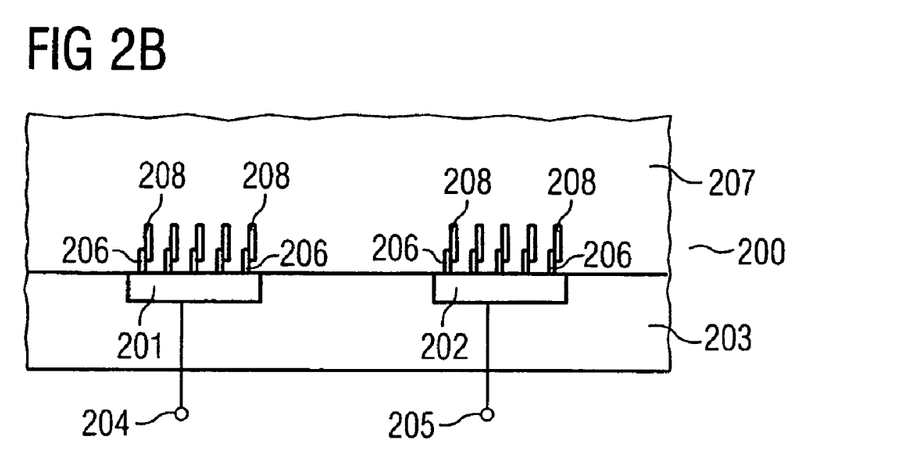

FIG. 2a and FIG. 2b show such a sensor as is described in R. Hintsche et al. and P. van Gerwen. The sensor 200 has two electrodes 201, 202 made of gold, which are embedded in an insulator layer 203 made of insulator material. Electrode connections 204, 205 are connected to the electrodes 201, 202, and the electrical potential present at the electrode 201, 202 can be fed to said electrode connections. The electrodes 201, 202 are arranged as planar electrodes. DNA probe molecules 206 are immobilized on each electrode 201, 202 (cf. FIG. 2a). The immobilization is effected in accordance with so-called gold-sulfur coupling. The analyte 207 to be examined is applied on the electrodes 201, 202. In this case, the analyte may be for example an electrolytic solution of different DNA sequences.

If the analyte 207 contains DNA strands 208 having a sequence which is complementary to the sequence of the DNA probe molecules 206, then said DNA strands 208 hybridize with the DNA probe molecules 206 (cf. FIG. 2b).

Hybridization of a DNA probe molecule 206 and a DNA strand 208 takes place only when the sequences of the respective DNA probe molecule 206 and of the corresponding DNA strand 208 are complementary to one another. If this is not the case, hybridization does not take place. Consequently, a DNA probe molecule of a predetermined sequence is in each case only able to bind, i.e. hybridize with, a specific DNA strand, namely the DNA strand having a respectively complementary sequence.

If hybridization takes place, then, in addition to other electrical parameters, the capacitance between the electrodes also changes, as can be seen from FIG. 2b. This change in capacitance can be used as a measurement quantity for detecting DNA molecules.

N. L. Thompson, B. C. Lagerholm, Total Internal Reflection Fluorescence: Applications in Cellular Biophysics, Current Opinion in Biotechnology, Vol. 8, pp. 58-64, 1997, discloses a further procedure for examining the electrolyte for the existence of a DNA strand having a predetermined sequence. In this procedure, the DNA strands of the desired sequence are marked with a fluorescent dye and their existence is determined on the basis of the fluorescence properties of the marked molecules. For this purpose, light in the visible or ultraviolet wavelength range is radiated onto the electrolyte and the fluorescent light emitted by the analyte, in particular by the marked DNA strand to be detected, is detected. The fluorescence behavior, i.e. in particular the emitted light beams that are detected, are taken as a basis for determining whether or not the DNA strand having the correspondingly predetermined sequence that is to be detected is contained in the analyte.

This procedure is very complicated since very precise knowledge about the fluorescence behavior of corresponding marker molecule at the DNA strand is necessary and, moreover, a marking reaction of the DNA strands is required before the beginning of the method. Furthermore, a very precise adjustment of the detection means for detecting the emitted light beams is necessary in order that the light beams can actually be detected.

Consequently, this procedure is expensive, complicated and very sensitive to disturbance influences, as a result of which the measurement result can very easily be corrupted.

Moreover, a reduction/oxidation recycling method for detecting macromolecular biopolymers is disclosed in R. Hintsche et al. and M. Paeschke et al.

The reduction/oxidation recycling method, also referred to as redox recycling method hereinafter, is explained in more detail below with reference to FIG. 4a to FIG. 4c.

Figure 4A:
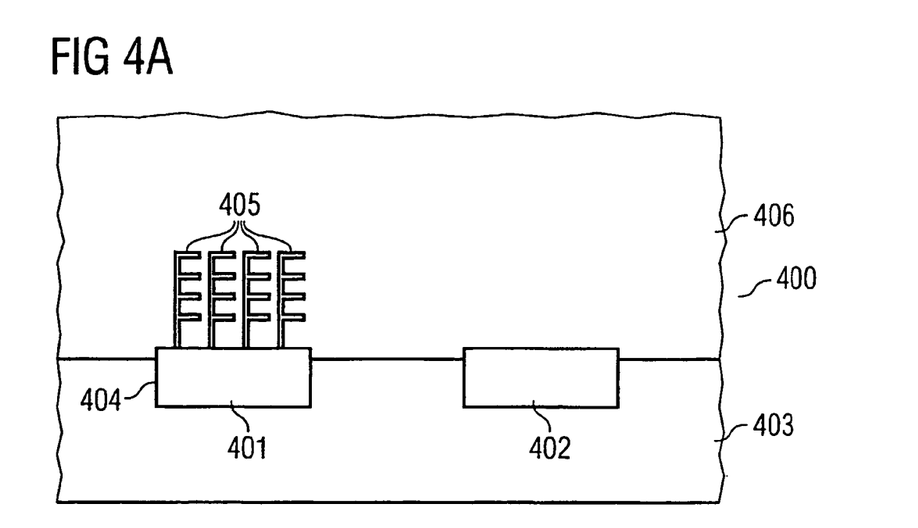
FIGS. 4a to 4c show sketches of a biosensor according to the prior art, on the basis of which individual states in the context of the redox recycling process are elucidated.

FIG. 4a shows a biosensor 400 having a first electrode 401 and a second electrode 402, which are applied on a substrate 403 as insulator layer.

A holding region, configured as a holding layer 404, is applied on the first electrode 401 made of gold. The holding region serves for immobilizing DNA probe molecules 405 on the first electrode 401.

No such holding region is provided on the second electrode.

If the biosensor 400 is intended to be used to detect DNA strands having a sequence which is complementary to the sequence of the DNA probe molecules 405, then the sensor 400 is brought into contact with a solution 406 to be examined in such a way that DNA strands having the complementary sequence that are possibly contained in the solution 406 to be examined can hybridize to the sequence of the DNA probe molecules 405.

Figure 4B:
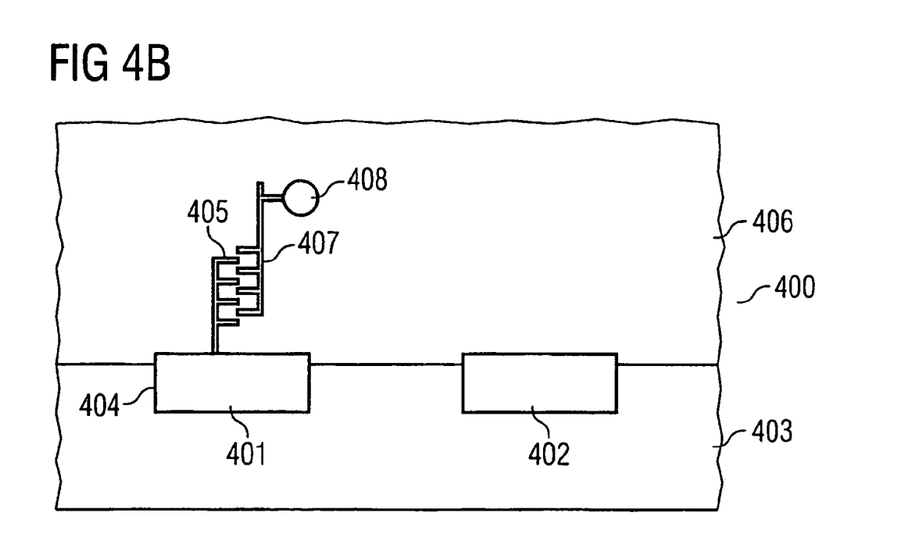

FIG. 4b shows the case where the DNA strands 407 to be detected are contained in the solution 406 to be examined and have hybridized to the DNA probe molecules 405.

The DNA strands 407 in the solution to be examined are marked with an enzyme 408, which enables molecules that are described below to be cleaved into partial molecules.

The number of DNA probe molecules 405 provided is usually considerably greater than the number of DNA strands 407 to be determined which are contained in the solution 406 to be examined.

Once the DNA strands 407 with the enzyme 408 that are possibly contained in the solution 406 to be examined have hybridized with the immobilized DNA probe molecules, the biosensor 400 is rinsed, as a result of which the non-hybridized DNA strands are removed and the biosensor 400 is cleaned of the solution 406 to be examined.

An electrically uncharged substance is added to this rinsing solution used for rinsing or a further solution 412 supplied separately in a further phase, said substance containing molecules which can be cleaved into a first partial molecule having a negative first electrical charge and into a second partial molecule having a positive second electrical charge by the enzyme at the hybridized DNA strands 407.

Figure 4C:
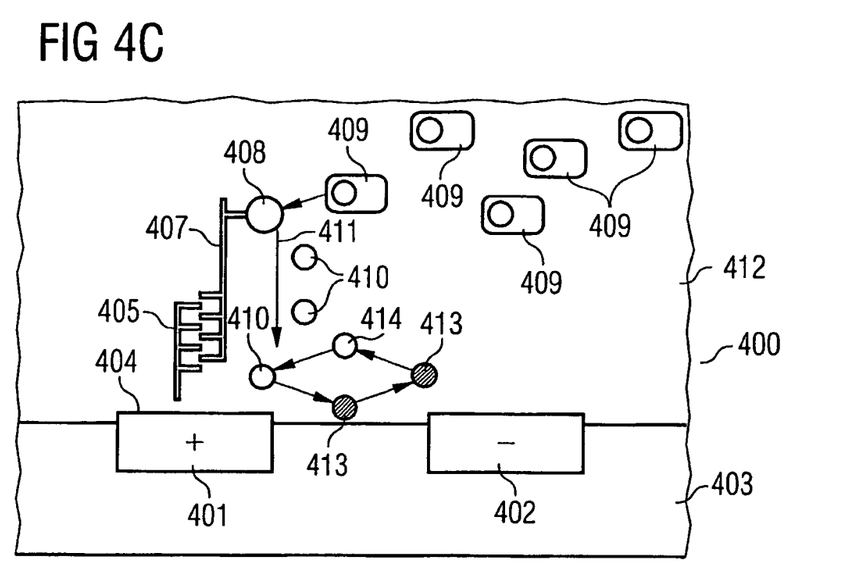

As is shown in FIG. 4c, the negatively charged partial molecules are attracted to the positively charged anode, as is indicated by the arrow 411 in FIG. 4c.

The negatively charged first partial molecules 410 are oxidized at the first electrode 401, which, as the anode, has a positive electrical potential, and are attracted as oxidized partial molecules 413 to the negatively charged cathode, i.e. the second electrode 402, where they are reduced again.

The reduced partial molecules 414 in turn migrate to the first electrode 401, i.e. to the anode.

An electrical circulating current is generated in this way, this current being approximately proportional to the number of charge carriers respectively generated by the enzymes 408.

Figure 5:
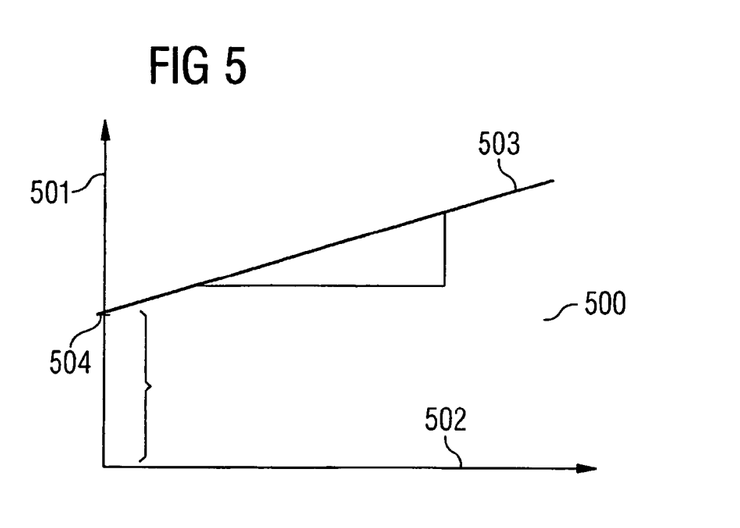
FIG. 5 shows a functional profile of a circulating current according to the prior art in the context of a redox recycling process.

The electrical parameter which is evaluated in this method is the change in the electrical current $$\frac{dI}{dt}$$

as a function of time t, as is illustrated in the diagram 500 in FIG. 5.

Figure 6A:
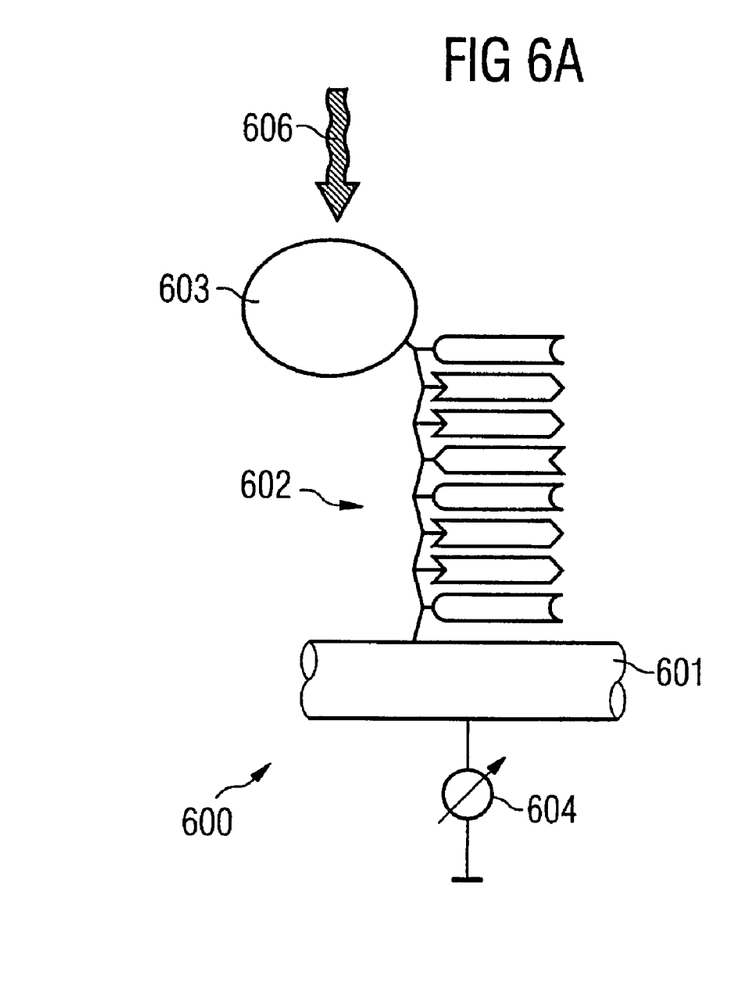
FIGS. 6a to 6c show the method for detecting nucleic acids that is disclosed in M. Paeschke et al.

Finally, e.g., WO 00/42217 A1 discloses a method which, as explained in more detail with reference to FIG. 6, is based on the difference in conductivity of single-stranded and double-stranded nucleic acid molecules and therefore resorts to a measurement of an electrical current or of a voltage.

In the method according to WO 00/42217 A1, a single-stranded nucleic acid molecule 602 is immobilized as capture molecule on an electrically conductive sensor surface 601. The capture molecule 602 carries a marking 603, which can emit or take up electrons during a light-inducible redox process.

Figure 6B:
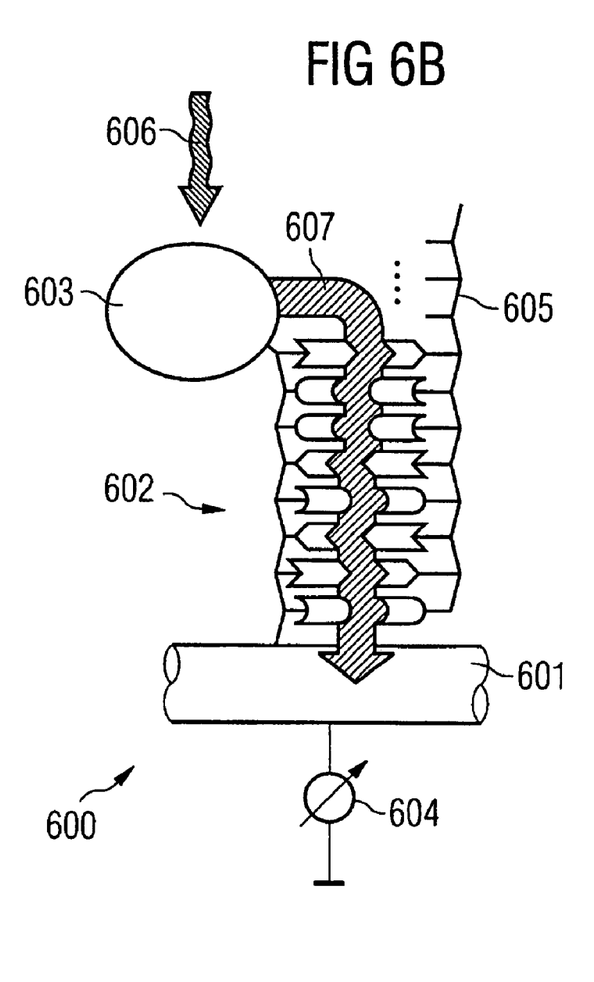

If light having a suitable wavelength, as symbolized by the arrow 606, is radiated onto the sensor 600, then the redox-active marking 603, excited by the light radiated in, continuously liberates electrons. If the marking is present in a double-stranded hybrid comprising DNA capture molecules 602 and nucleic acids 605 to be detected, this double-stranded hybrid acts as a type of electron pump and conducts electrons, as illustrated by the arrow 607, from the marking 603 to the conductive surface 601, so that a current can be measured at said surface by means of a measuring device 604 (cf. FIGS. 6a, b). However, if no hybridization is effected, single-stranded capture molecules 602 approximately constitute an insulator; consequently, no current flows at the surface 601.

Figure 6C:
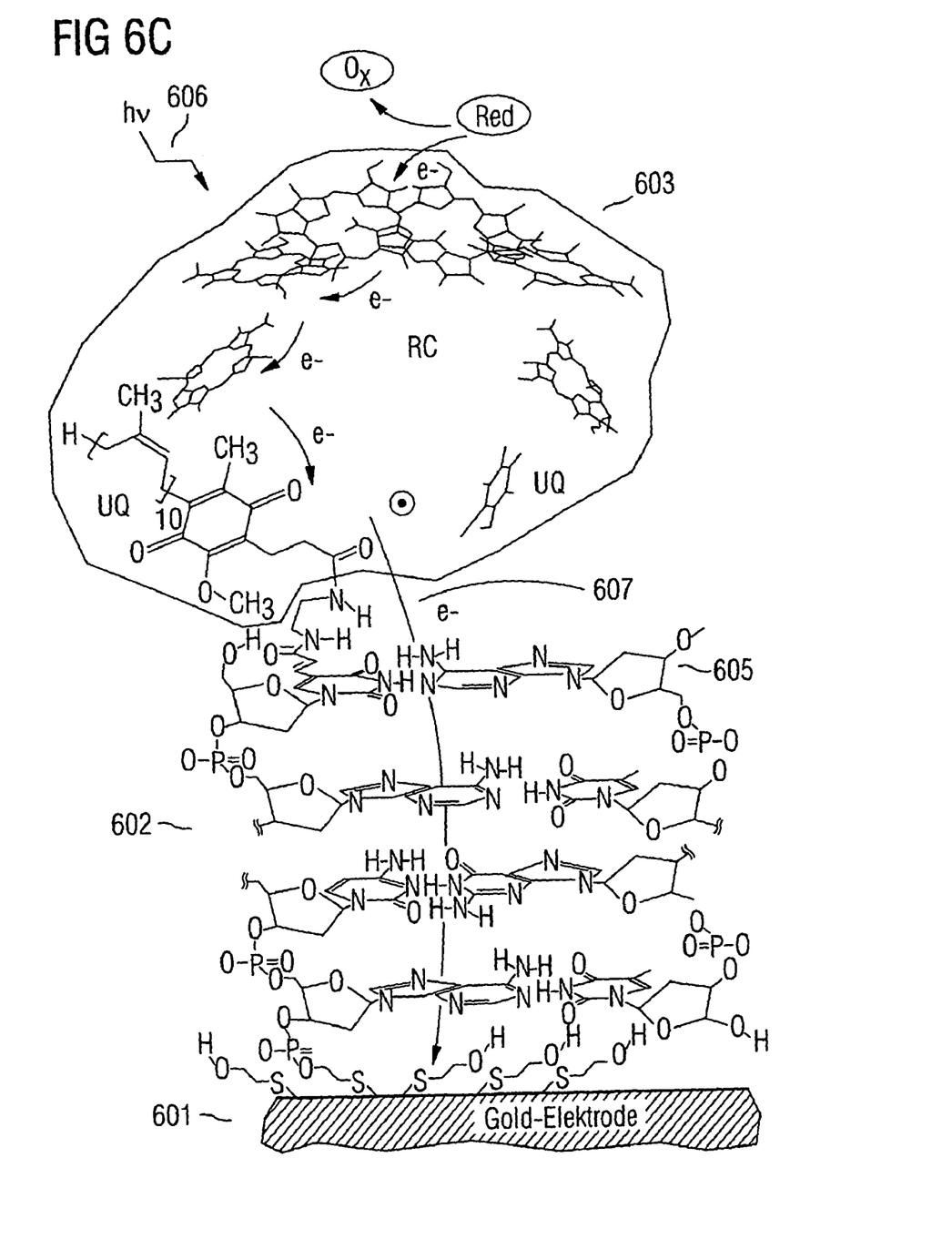

FIG. 6c, corresponding to FIG. 4 from WO 00/42217 A1, shows an illustration which is more precise in molecular detail and in which a photosynthetic bacterial reaction center is used as redox-active marking.

The abovementioned methods for detecting macromolecular biopolymers such as nucleic acids have in common the disadvantage that their detection sensitivity is relatively low, in particular if only small amounts of molecules to be detected are available.

DE 199 40 810 A1 discloses a method and a measuring device for determining a multiplicity of analytes in a sample.

WO 01/75151 A2 discloses a method for detecting macromolecular biopolymers using an electrode arrangement.

DE 199 16 921 A1 discloses an electrical sensor array based on voltametric and/or impedimetric detection principles with serial or parallel read-out.

WO 94/05414 A1 discloses an integrated instrument for manipulation, carrying out of a reaction and detection of samples in microliter to picoliter dimensions.

U.S. Pat. No. 5,648,213 discloses structures and methods for use in the detection of analytes.

SUMMARY OF THE INVENTION

The invention is based on the problem of providing a method for increasing the sensitivity and also an apparatus for the detection of macromolecular biopolymers.

The problem is solved by means of the methods and also the biosensor having the features in accordance with the independent patent claims.

The first method for detecting macromolecular biopolymers uses at least one unit for immobilizing macromolecular biopolymers. This unit is provided with first molecules which serve as capture molecules. In the method, a sample is brought into contact with the at least one unit for immobilizing macromolecular biopolymers. In this case, the sample may contain the macromolecular biopolymers (that are preferably to be detected) and the macromolecular biopolymers or the first molecules in this case have a marking which can be used to generate a detectable signal, for example an optical signal. Macromolecular biopolymers contained in the sample are bound to the capture molecules, thereby forming complexes comprising capture molecules and macromolecular biopolymers. Afterwards, the marking is used to excite the emission of a signal, for example fluorescent light, this signal emitted by means of the marking is detected, and the complexes comprising capture molecules and macromolecular biopolymers are separated (again) for example by means of thermal denaturing. This separation abruptly alters the intensity of the emitted signal. The macromolecular biopolymers are then detected by means of the intensity, preferably by means of the change in intensity of the signal.

A second method for detecting macromolecular biopolymers uses an electrode arrangement having at least one unit for immobilizing macromolecular biopolymers.

For the method, the at least one unit for immobilizing macromolecular biopolymers is provided with first molecules which serve as capture molecules. A sample is then brought into contact with the at least one immobilization unit, it being possible for the sample to contain macromolecular biopolymers to be detected. In the method, macromolecular biopolymers which are contained in the sample and complementary to the capture molecules are bound to the capture molecules. Complexes comprising capture molecules and macromolecular biopolymers are thereby formed. The change in the electrical signal during the complexing phase (i.e. for example the hybridization phase if capture molecules and macromolecular biopolymers are nucleic acid molecules) is detected, in particular the measured value at the end of the complexing phase being retained as output value. Furthermore, in the method, a first electrical measurement is carried out, preferably after the at least one immobilization unit is brought into contact with the sample to be examined. The complexes comprising capture molecules and macromolecular biopolyers, such as e.g. double-stranded hybrid molecules comprising nucleic acids, are then separated for example by means of thermal denaturing. This brings about a spontaneous alteration of the value of the electrical measurement. A second electrical measurement is carried out at that point or precisely starting from the separation. The nucleic acid molecules are detected using the result of the electrical measurement, e.g. on the basis of the difference between the value of the first measurement and the value of the second measurement.

To put it clearly, the methods of the invention are based on the insight that the separation of macromolecular biopolymers such as e.g. double-stranded nucleic acid molecules, i.e. the denaturing or melting of nucleic acid molecules, is a cooperative ("abrupt") process and the denaturing therefore brings about an abrupt change in a measured value or a signal, which can be used to detect macromolecular biopolymers such as nucleic acids.

By virtue of the detection of precisely this abrupt change, the present methods have the advantage over the known methods of improved detection sensitivity, particularly if only small amounts of biopolymers to be detected are present. This is because, precisely in the case of a small signal as seen in absolute terms, it is more precise to measure a single abrupt change than a continuous slow change, as takes place e.g. in the method from P. van Gerwen, which is based on a change in capacitance during the hybridization process.

Macromolecular biopolymers which can be detected with the aid of the present methods are all those which, with at least one binding partner form a complex reversibly, in the case of which the interactions between the binding partners (i.e. here a macromolecular biopolymer and its corresponding capture molecule) are broken up in an abruptly proceeding, preferably cooperative, process. Examples of such macromolecular biopolymers are nucleic acids which can form double-stranded complexes with complementary nucleic acid molecules or molecules such as antibodies or antibody fragments, receptors, peptides, aptamers, alternative scaffolds, phage display libraries, RNA/DNA fusions, which can form such complexes with corresponding binding partners.

The invention is explained in more detail below predominantly on the basis of nucleic acids as macromolecular biopolymers to be detected. However, the invention is not restricted to nucleic acids, but rather can be applied generally to any type of molecular system which exhibits an abrupt, e.g. thermally induced, phase transition in the sense of the invention which can be evaluated electrically or optically.

The denaturing, i.e. the separation of the hybrid molecules comprising capture molecules and nucleic acid molecules to be detected, can be achieved in the methods of the invention by all measures which lead to a cooperative breakage of the hydrogen bridges between the respectively complementary nucleotide pairs. The denaturing is preferably effected by increasing the temperature to a temperature which lies above the melting point (Tm) of the double-stranded hybrid molecules. However, it is also possible to achieve the melting of the double-stranded nucleic acid molecules by altering the pH value, i.e. in particular by adding alkali, and/or by adding organic (aprotic) solvents such as DMSO of DMF, or by increasing the ionic strength (i.e. preferably by increasing the salt concentration). The melting point Tm used for carrying out the present methods can be determined experimentally and/or be estimated by familiar methods (in this respect, see e.g. J. G. Wetmur, DNA Probes: Applications of the Principles of Nucleic Acid Hybridization, Critical Reviews in Biochemistry and Molecular Biology, 26(3/4):227-259 (1991)).

In the sense of the invention, detection is understood to be both the qualitative and the quantitative detection of biopolymers such as nucleic acid molecules in an analyte to be examined. This means that the term "detection" likewise includes ascertaining the absence of biopolymers such as nucleic acid molecules in the analyte. In the sense of the invention, said analyte may be a sample to be examined which is added to the immobilized capture molecules. On the other hand, the analyte may, however, also contain the capture molecules, which are then immobilized and detected with the aid of the added macromolecular biopolymers.

In order to form the double-stranded hybrid molecules, the first nucleic acid molecules serving as capture molecules are preferably single-stranded molecules. However, it is also possible to use double-stranded molecules as capture molecules which have only a single-stranded area whose sequence is complementary to the nucleotide sequence of the nucleic acid molecules to be detected. A further possibility is to form the double-stranded hybrid by inducing a fluid motion perpendicular to the at least one immobilization unit, as described e.g. in E. Braun et al., DNA-templated assembly and electrode attachment of a conducting silver wire, Nature, Vol. 391, pp. 775-778, 1998. In this case, the capture molecule may initially also be present completely as a double strand.

In the case of the first method described here, a signal is generated by means of the marking situated at the nucleic acid molecules or the capture molecules.

In a refinement of this method, such a signal is an electrical current or an altered impedance, in particular capacitance or conductivity in the region of the sensor structure. In a further refinement, the signal is visible light or UV light.

This reveals that different types of marking, a marking also being referred to as a reporter group below, can be used in this method.

Thus, the marking may be a (chemical) compound or group which, through external excitation, can directly generate a signal that can be used for detecting the nucleic acid molecules. Examples of such markings are fluorescent dyes (fluorophores) or compounds which can initiate a chemiluminescence reaction. Another group of such markings are redox-active enzymes as are described e.g. in WO 00/42217 A1, which, after light having a suitable wavelength has been radiated in, generate an electron flow through double-stranded nucleic acid molecules, which electron flow can be measured.

Such a redox-active marking in the sense of the invention consequently comprises the chemically inducible or photo-inducible redox-active units defined in [6] (cf. the definition of the photo-inducible redox-active unit in WO 00/42217 A1 on page 10, 2nd paragraph, to page 12, 2nd paragraph, or the chemically inducible redox-active unit on page 12, 2nd paragraph, page 13, 1st paragraph) which are bound (covalently) via at least one bond to a nucleic acid single-stranded molecule serving as capture molecule.

Consequently, examples of photo-inducible redox-active markings that can be used here are the photosynthetic bacterial reaction center (RC), cyclophanes or an at least bimolecular electron-donor/electron-acceptor complex in its meaning in accordance with WO 00/42217 A1 (see page 14, 2nd paragraph, page 15, 1st paragraph, therein).

Examples of chemically inducible redox-active markings are therefore the cytochrome bc complex, the cytochrome $c_2$ complex of the photosynthesis-driving bacteria or chemically inducible at least bimolecular electron-donor/electron-acceptor complexes such as suitable cyclophanes (see WO 00/42217 A1, page 31, 2nd paragraph).

It should be noted here that the redox-active markings just described are to be differentiated from markings such as enzymes which can be used in the reduction/oxidation recycling method that can likewise be employed here. It should furthermore be noted that the redox-active markings are preferably used in the method in which the capture molecules carry a marking.

On the other hand, the marking may be a substance which only indirectly generates a signal for detecting the biopolymers such as nucleic passive molecules i.e. a substance which instigates the generation of the signal. Such a reporter group may be for example an enzyme which catalyzes a chemical reaction which is then used to detect the biopolymers. Examples of such enzymes are alkaline phosphatase, glutathione-S-transferase, superoxide dismutase, horseradish perioxidase, alpha-galaktosidase and beta-galaktosidase. These enzymes are able to cleave suitable substrates which produce colored end products or e.g. compounds which can be used in the reduction/oxidation recycling method described above. The group of markings which only indirectly generate a signal that can be used for detecting macromolecular biopolymers furthermore includes ligands for binding proteins and substrates for enzymes. These markings are referred to generally here as enzyme ligands. Examples of such enzyme ligands that can be used as a marking are biotin, streptavidin, avidin, digoxigenin or substrates for the enzymes mentioned above.

This differentiation between markings that indirectly and directly generate a signal shall be illustrated in detail with reference to the generation of a chemiluminescence signal.

One marking which can intrinsically (i.e. directly in the present sense) effect the generation of chemiluminescence radiation is e.g. horseradish peroxidase, which, in the presence of hydrogen peroxide ($H_2O_2$), catalyzes the oxidation of cyclic diacyl hydrazides such as luminol. During this chemical reaction, a reaction product is formed in an excited state which undergoes transition to the ground state through light emission. This light emission can be amplified by further chemical reactants, e.g. by 4-iodphenol in the case of the peroxidase-luminol system. A further example is the luciferase of *Photinus pyralis*, which, in the presence of ATP and oxygen, catalyzes the conversion of luciferin into oxidized luciferin with light emission. Another example is alkaline phosphatase using suitable 1,2-dioxetanes as substrates; cf. Roche Molecular Biochemicals, 1999 Biochemicals Catalog, p. 99. Such a marking may, as desired, be linked directly to one of the two binding partners (capture molecule or biopolymer).

However, it is also possible, on the other hand, for the marking used to be a chemical compound which itself cannot initiate a chemiluminescence reaction but has specific binding affinity with a binding partner, which, for its part, is coupled e.g. to an enzyme such as horseradish peroxidase. Such a marking is e.g. biotin. The latter has a high binding affinity with the protein streptavidin. If streptavidin is coupled e.g. to the abovementioned horseradish peroxidase, this reagent is able on the one hand to bind to biotin which has been incorporated as a marking e.g. into a biopolymer to be detected, and on the other hand initiate a chemiluminescence reaction. Therefore, the components listed above such as biotin, avidin or digoxigenin can also be used in the present case as marking/marking component of the capture molecules or biopolymers to be detected. The use of these markings that work indirectly may be advantageous since, figuratively, they are situated at the start of a signal amplifying cascade and therefore can additionally increase the detection sensitivity of the method.

In the case of the method that operates on the basis of an electrode arrangement (and therefore does not require a marking of the kind just described), in one refinement, the potential present at an electrode is measured during the electrical measurement. In other refinements, the capacitance, the electrical resistance, the electrical current flow or the impedance between two electrodes or the change in the corresponding value of these measurement quantities is measured.

These electrical measurements described above may be based, inter alia, on the fact that nucleic acids in solution are generally polyanions. The denaturing (the separation into the single-stranded immobilized capture molecules and the nucleic acid molecules to be detected) therefore leads to a diffusion-dictated charge separation. To put it clearly, this approximately corresponds to the discharging process of a charged capacitor, which can be detected by means of a suitable sensor unit. In the case of the method based on an electrode arrangement, it is not only advantageous that a preceding marking of the nucleic acid to be detected is not necessary; rather, it is also advantageous that, as a result of the collective (cooperative) charge transfer, it is possible to detect e.g. a comparatively large current flow or a comparatively large change in capacitance using one electrode. This enables a high measurement sensitivity. Therefore, this method holds advantages particularly for a quantitative determination of the nucleic acid molecules to be detected.

The charge transfer just described also results in a change in the electrochemical potential which forms at the interface between the immobilization unit and the medium (to be examined). In a further embodiment of the second method, this electrical interface potential is therefore measured for the detection of nucleic acids.

In a refinement of both methods in which the denaturing is effected thermally, the temperature measurement and/or the temperature control are performed by a thermostatically regulating unit integrated into the biosensor having the at least one immobilization unit. The thermostatically regulating unit may be connected to an external control and monitoring unit. However, it may also itself have all the monitoring and control units besides the heating elements. In the last-mentioned case, the entire temperature control is therefore effected on-chip.

This may be realized for example by integration of heating resistors, temperature sensors and/or regulating circuits.

The heating elements for temperature regulation should be in good thermal contact with the biosensor arrangement. This may be realized, as explained above, by integration of the heating resistor on the biochip or by a so-called off-chip heating resistor which is arranged outside the chip and integrated into the housing. The temperature sensors are preferably to be fitted in direct proximity to the nucleic acid molecules in order to enable to the temperature to be measured exactly and in a manner free of delay. The regulating circuit for temperature control may be embodied as a proportional, derivative and/or integral controller.

It is also possible, of course, to effect temperature control by thermal coupling from outside, e.g. by means of resistors integrated in a receptacle and/or holding device for the biosensor. One example thereof is resistors integrated in the housing of the biosensor.

In the sense of the invention, "immobilization unit" is understood to be a unit having a surface on which the nucleic acid molecules serving as capture molecules can be immobilized, i.e. to which the capture molecules can bind by physical or chemical interactions. Said interactions include hydrophobic or ionic (electrostatic) interactions and covalent bonds. Examples of suitable surface materials which can be used for the at least one immobilization unit are metals such as gold or silver, plastics such as polyethylene or polypropylene or inorganic substances such as silicon dioxide.

One example of a physical interaction which effects an immobilization of the capture molecules is absorption at the surface. This type of immobilization may take place for example if the immobilization means is a plastics material used for producing microtiter plates (e.g. polypropylene).

However, a covalent linkage of the capture molecules to the immobilization unit is preferred, because this enables the orientation of the capture molecules to be controlled. The covalent linkage may be effected by means of any suitable linker chemistry.

In a refinement of the two methods, the at least one immobilization unit is arranged adjacent to an operating electrode, i.e. the operating electrode is arranged in spatial proximity such that it can act on the immobilization unit or units via electrical forces/fields. The immobilization unit is preferably arranged above the operating electrode. In the sense of the invention, an operating electrode is understood to be an electrode which is actively involved in one of the detection methods described here, e.g. in that an electrical current which flows through said electrode is measured. An operating electrode in the sense of the invention is for example also an electrode to which a negative potential is applied, which promotes the separation of a double-stranded hybrid molecule into the two negatively charged single strands.

Such an operating electrode is to be differentiated from a monitoring electrode. A monitoring electrode is an electrode which is not actively involved in the detection of nucleic acids. By way of example, if an impedance measurement is carried out by means of the method based on an electrode arrangement, one of the two electrodes required for this purpose may serve exclusively as monitoring electrode. This is the case e.g. if the potential at the interface between the immobilization unit and a medium to be examined is used for detection purposes.

In the first of the two methods disclosed here, which operates with a marking, a reference electrode in the above sense may be entirely dispensed with if e.g. the measurement signal is optically detected by means of a fluorescence or chemiluminescence marking.

It shall be stated in summary at this junctive that a monitoring electrode is necessary only when absolute electrical potentials are intended to be applied or measured at the operating electrodes. The monitoring electrode, whose potential is measured in a manner free of current, supplies the reference-ground potential here. In pure electrochemical methods (e.g. redox recycling) such an electrode is absolutely necessary for measurement purposes. By contrast, a measuring electrode is not necessary if electric fields are used only for promoting the denaturing reaction. In this case, exact knowledge of the electrode potential is not absolutely necessary. In this connection, it should be noted that such an electrode used for promoting the complexing or denaturing may e.g. also be used when optically detecting the signal.

In a further embodiment of the methods, the at least one immobilization unit is applied directly on an operating electrode. In a further refinement of the methods, the at least one unit is applied on a photodiode.

In another refinement, the at least one immobilization unit is configured as an operating electrode.

As already mentioned above, in the methods described here a negative electrical potential may be applied to the operating electrode for the purpose of separating the hybrid molecules. This additionally reinforces the collectivity of the denaturing process and thus further improves the measurement accuracy and/or measurement sensitivity.

In a further embodiment of the two methods, a positive electrical potential may be applied to one or more operating electrodes, either before or after the capture molecules have been brought into contact with the medium to be examined. This positive electrical potential can accelerate the normally diffusion-driven hybridization process in that the negatively charged nucleic acid molecules are attracted to the at least one immobilization unit by suitable electric fields. It is also possible, of course, depending on the respective sensor construction, to use a plurality of electrodes for this purpose. Furthermore, it is also possible, of course, for that operating electrode or those operating electrodes used for accelerating the melting process also to be used for accelerating the habitization process.

In both of the methods disclosed here, it is possible to use a plurality of units for immobilizing nucleic acids, it being possible for these units to be arranged in a regular arrangement, an array.

The biosensor described here for detecting nucleic acid molecules has at least one unit for immobilizing nucleic acids, a detection unit and also a thermostatically regulating unit integrated into the sensor. The detection unit is configured in such a way that nucleic acid molecules bound to capture molecules applied on the immobilization unit are detected by means of the detection unit.

A detection unit in the sense of the invention is a unit which can detect and forward a signal emitted by a marking at the nucleic acid molecules, or which can detect and forward an electrical measurement quantity which is influenced by the presence or absence of (double-stranded) nucleic acid molecules. Examples of such a detection unit are a photodiode, an electrode pair or a MOSFET. As an alternative, however, the detection unit may also be realized off-chip, for example as an optical detector (CCD camera) in the read-out/operating device for the sensor according to the invention.

The term "integrated into the sensor" is to be understood here to mean that the thermostatically regulating unit is part of the actual sensor. This means that the thermostatically regulating unit is not accommodated in an external receptacle or holding device such as a housing for the biosensor.

The thermostatically regulating unit integrated in the sensor serves for denaturing and/or hybridization and/or control of the binding behavior (attraction, binding or repulsion of molecules, for example thermal control of the linker chemistry) of the double-stranded hybrid molecules. It may have e.g. conventional heating elements such as electrical heating resistors and also the control and measuring units required for monitoring the temperature. Furthermore, the thermostatically regulating unit may be used for synthesis and/or duplication for example via polymerase chain reaction (PCR). Furthermore, the thermostatically regulating unit may be used to accelerate the reaction process in that the temperature can be used to control the convection and thus the diffusion rate in the reaction space.

In one development, the biosensor has at least one operating electrode. The latter is arranged adjacent to the at least one immobilization unit, so that the unit is influenced by an electrical potential or field of said operating electrode. The above-described acceleration of the formation of the hybrid molecule or the denaturing process can be carried out in this way. The at least one immobilization unit is preferably arranged above the operating electrode.

In another refinement of the biosensor, the at least one immobilization unit is applied on an operating electrode or a photodiode. The immobilization unit may be applied e.g. on a CMOS chip. In the case of a marking that can be evaluated optically, the at least one immobilization unit may also be applied on a CMOS camera or a CCD.

In a further refinement of the biosensor, the at least one immobilization unit is configured as an operating electrode.

In a further embodiment, the apparatus has a plurality of units for immobilizing macromolecular biopolymers in a regular arrangement (an array).

In this connection, nucleic acid molecules are understood to be for example (longer-chain) DNA molecules and RNA molecules, PNA molecules, cDNA molecules, or else shorter oligonucleotides with, for example, 10 to 50 base pairs (bp), in particular 10 to 30 base pairs. The nucleic acids may be double-stranded, but may also have at least single-stranded areas or be present as single strands for example as a result of preceding thermal denaturing (strand separation) for their detection. In this case, the sequence of the nucleic acids to be detected may be at least partly or completely predetermined, i.e. known.

If nucleic acid molecules of a predetermined nucleotide sequence are detected by the method described here, then they are preferably detected in signal-stranded form, i.e. they are converted into single strands if appropriate prior to the detection, by denaturing. In this case, the capture molecules used are nucleic acid molecules having a sequence that is complementary to the single-stranded area. These nucleic acid capture molecules may in turn be nucleic acid molecules having approximately 20 bp to approximately 50 bp or else have longer nucleotide sequences having up to approximately 500 bp or longer, as long as they do not form any intermolecular structures preventing hybridization of the capture molecule to the nucleic acid to be detected.

The present methods make it possible, of course, not just to detect a single type of nucleic acid molecules in an individual measurement series; rather, a plurality of nucleic acid molecules can be detected simultaneously or else successively. For this purpose, a plurality of types of capture molecules, each of which has a (specific) binding affinity for a specific nucleic acid molecule to be detected, may be bound on the immobilization unit, and/or a plurality of immobilization units may be used, only one type of capture molecule being bound to each of said units. In the case of these multiple determinations, if markings are used for detection purposes, a marking that can be differentiated from the other markings is preferably used for each nucleic acid molecule to be detected. By way of example, two or more fluorophores may be used as markings, each of said fluorophores preferably having a specific excitation and emission wavelength.

In the methods disclosed here, in a first method step in each case the at least one immobilization unit is provided with the capture molecules.

A sample to be examined, preferably a liquid medium such as an electrolyte, is then brought into contact with the immobilization unit. This is done in such a way that the nucleic acid molecules can bind to the capture molecules, i.e. at a temperature below the melting point of the double-stranded hybrid molecules. For the case where the medium contains a plurality of nucleic acids to be detected, the conditions are chosen such that these can bind here in each case at the same time or successively to their corresponding capture molecule in order to form the double-stranded hybrid molecules.

Afterwards, non-hybridized nucleic acid molecules to be detected can be removed from the reaction space by means of a suitable washing step.

In the first method, in order to detect the nucleic acids, the corresponding marking is then excited to emit a signal and the signal is detected. For this purpose, e.g. an emitted fluorescent radiation or electrical current caused by the redox recycling described above is measured.

A single reference measurement may be carried out although it is more expedient to carry out a continuous measurement/detection of the emitted signal through to the end of the method. At the beginning of the measurement (or else earlier or later), the temperature in the reaction space, i.e. at least at the surface of the at least one immobilization unit, is increased up to a temperature above the melting point of the double-stranded hybrid molecules. The denaturing may e.g. also be achieved by pulsed alteration of the pH value. If the melting point is reached, then the intensity of the signal changes abruptly as a result of the denaturing, that is to say that a fall to zero ideally occurs since the nucleic acid molecules to be detected are now freely present in solution again and removed by diffusion from the reaction space observed. The removal of the single-stranded molecules from the surface of the immobilization unit can be intensified and accelerated by application of a convection current.

This signal alteration is used for detection purposes in the present case.

The same method steps are carried out, in principle, in the second method of the invention.

In the second method, it is possible to use various electrode arrangements having at least one immobilization unit. Examples of electrode arrangements that can be used here are electrically conductive lattices or networks, electrically conductive porous materials, a plate electrode arrangement or an inter-digital electrode arrangement, as known from R. Hintsche et al. In the case of an interdigital electrode arrangement, a plurality or all of the "fingers" of the arrangement may be provided with immobilization units or themselves be configured as said units.

Furthermore, various arrangements of connecting electrodes in parallel in the electrode arrangement may be provided; for example, the electrodes may be configured as cylindrical elements which are respectively arranged concentrically around one another and are electrically insulated from one another for example by means of a suitable dielectric, so that an electric field forms between the electrodes.

In a preferred measurement method, a plurality of hybridization/denaturing cycles are carried out using the sensor according to the invention. The spontaneous signal change that takes place periodically as a result can be utilized for further increasing the sensitivity and measurement accuracy in that the measurement results of a plurality of cycles are recorded and subsequently evaluated statistically; for example the statistical mean value may be formed.

BRIEF DESCRIPTION OF THE DRAWINGS

Exemplary embodiments of the invention are illustrated in the figures and are explained in more detail below.

DETAILED DESCRIPTION OF THE PREFERRED MODE OF THE INVENTION

FIG. 1 shows a detail from a biosensor 100 which can be used to carry out a first exemplary embodiment of the method described here.

Figure 1A:
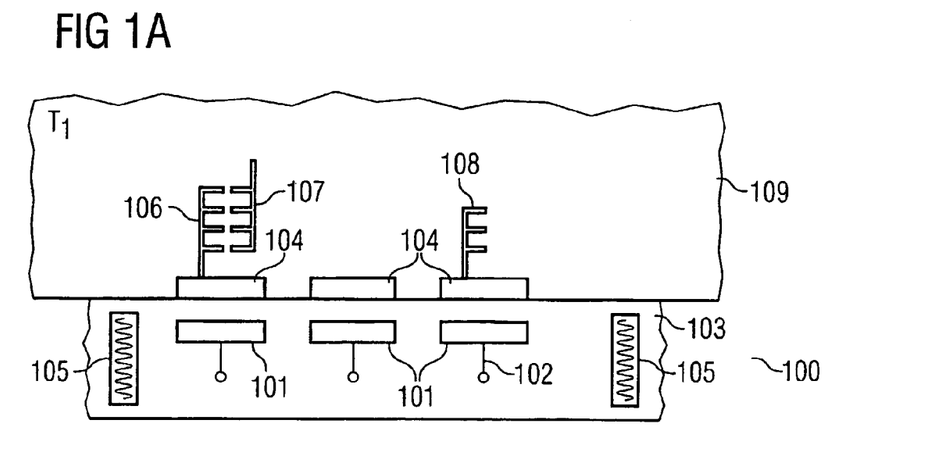
FIGS. 1a and 1b show an embodiment of a biosensor according to the invention and this biosensor at different method states in one of the methods disclosed here.

FIG. 1a shows the biosensor 100 having a plurality of electrodes 101, which are respectively connected via an electrical connection 102 to an evaluation unit (not illustrated). The electrodes are embedded in an insulator layer 103 made of insulator material. Units 104 for immobilizing nucleic acids are applied on the insulator layer and above the electrodes 101. The biosensor 100 furthermore has, embedded into the "sensor substrate", a thermostatically regulating unit 105 serving for temperature control.

The sensor 100 is an example of a sensor in which the electrodes only serve for detecting the nucleic acid molecules on the basis of a change in an electric field that is induced by the melting of the double-stranded hybrid molecules.

The immobilization units 104 of the sensor 100 are produced from gold.

As an alternative, the immobilization units 104 may also be produced from silicon oxide and may be coated with a material which is suitable for immobilizing capture molecules.

By way of example, it is possible to use known alkoxysilane derivatives such as
3-glycidoxypropylmethyloxysilane,
3-acetoxypropyltrimethoxysilane,
3-aminopropyltriethoxysilane,
4-(hydroxybutyramido)propyltriethoxysilane,
3-N,N-bis(2-hydroxyethyl)aminopropyltriethoxysilane,
or other related types of materials which are able, with one of their termini, to enter into a bond, for example a covalent bond, with the surface of the silicon oxide and, with their other terminus, to offer the nucleic acid molecule to be immobilized a chemically reactive group such as an epoxy, acetoxy, amine or hydroxyl radical for reaction.

As an alternative, it is possible to use poly-L-lysine, for example.

If a capture molecule to be immobilized reacts with such an activated group, then it is bound via the chosen material as a type of covalent linker on the surface of the coating on the immobilization unit.

DNA probe molecules 106 and 108 are applied as capture molecules on the immobilization unit 104. In this case, the first DNA probe molecules 106 have a sequence that is complementary to a predetermined first DNA sequence. The second capture molecules 108 have a nucleotide sequence that is complementary to a second predetermined DNA sequence. The capture molecules 106 and 108 are immobilized by means of the so-called gold-sulfur coupling.

Sequences of the DNA strands that are respectively complementary to the sequences of the probe molecules can hybridize to the purine bases adenine (A), guanine (G), and the pyrimidine bases thymine (T) or cytosine (C), in the customary manner, i.e. by base pairing via hydrogen bridge bonds between A and T and between C and G, respectively. When other nucleic acid molecules are used, other bases are correspondingly used, for example uridine (U) in the case of an RNA molecule.

FIG. 1a furthermore shows an electrolyte 109, which is brought into contact with the immobilization units 104 and the DNA probe molecules 106 and 108 at a temperature T1. In this case, the temperature T1 is below the melting point Tm of the double-stranded hybrid molecules comprising the capture molecules 106 and 108 with their nucleic acid molecules to be detected. The melting point Tm given under the test conditions is determined experimentally or estimated beforehand, if appropriate.

FIG. 1a shows the biosensor 100 for the case where the electrolyte 109 contains DNA molecules 107 having a predetermined first nucleotide sequence that is complementary to the sequence of the first DNA probe molecules 106. In this case, the DNA strands 107 that are complementary to the first DNA probe molecules 106 hybridize with the first DNA probe molecules 106 applied on the units 104.

Since the sequences of DNA strands hybridize only with the respectively specific complementary sequence, the DNA strands that are complementary to the first DNA probe molecules do not hybridize with the second DNA probe molecules 108.

A first electrical measurement is carried out at the electrodes 102 before or alternatively after hybridization. The potential present at the electrodes is preferably measured in this embodiment.

Figure 1B:
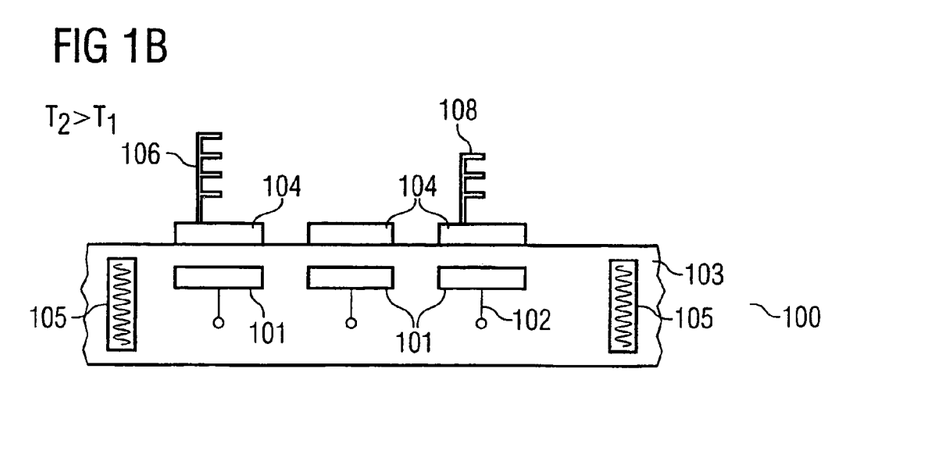

The result after hybridization has been effected is that double-stranded hybrid molecules are situated, i.e. double-stranded DNA molecules are immobilized, on one of the units 104. On the other unit 104, only the second DNA probe molecules 108 are present still as single-stranded molecules.

After an optional washing step, the temperature is continuously increased by means of the thermostatically regulating unit 105. The melting point Tm of the hybrid molecules comprising the capture molecules 106 and the molecules 107 to be detected is reached in the process. At this point in time, the double-stranded molecules are denatured, i.e. separated into the two single strands 106 and 107. On account of the polyanionic character of the nucleic acids, this dissociation brings about an abrupt charge separation, which is detected by means of a second potential measurement at the electrodes 102. The presence or absence of the DNA molecules 107 is determined by means of comparison of the values obtained for the potential in the two measurements. If the difference determined exceeds a (predetermined) threshold value, then it is inferred from this that the DNA molecules 107 were present in the sample, and if appropriate in what concentration. In the case of a difference below the threshold value, it is inferred from this that no DNA molecules 107 were present. This classification according to threshold value can also be carried out in the other methods disclosed here.

Figure 3A:
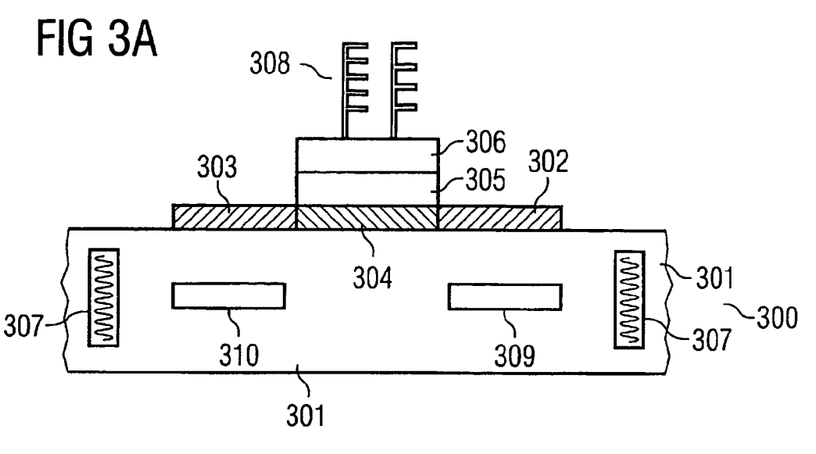
FIGS. 3a and 3b show further embodiments of a biosensor according to the invention, which can be used to carry out further types of implementation of the methods described here.

FIG. 3a shows a biosensor 300 provided with a MOSFET for the detection of the nucleic acid molecules.

The biosensor 300 has a substrate material 301, on which (for example n- or p-semiconducting) layers 302 and 303 are respectively situated as source and drain of a MOSFET. Furthermore, the sensor has a layer 304 serving as channel region. The oxide layer 305 of the MOSFET is situated on the channel region 304. A metallic gate 306 is applied on the oxide layer 305. Said gate is produced from gold and serves as a unit for immobilizing nucleic acids. Furthermore, the sensor has a unit 307 for temperature control. Capture molecules 308 are immobilized on the gate 306, for example by means of gold-sulfur coupling. The electrical connections of source, drain and gate of the MOSFET are not shown. The sensor 300 may (optionally) furthermore have further electrodes 309 and 310 adjacent to the MOSFET. The electrodes 309 and 310 do not serve for detecting the nucleic acid molecules, but rather are used to generate electric fields in order to promote the hybridization and denaturing process.

The method for detecting nucleic acid molecules as described with reference to FIG. 1 can be carried out with the aid of the biosensor 300. In this case, the gate 306 serves not only as an immobilization unit, but also as an "active" electrode, i.e. operating electrode in the sense of the invention. In the case of the biosensor 300, the charges immobilized on account of the hybrid formation generate an electric field which modulates the channel current of the MOSFET. Consequently, the current through the channel, which changes e.g. as a result of the denaturing, represents a direct measure of the quantity of charge situated on the immobilization unit 306. The change in this channel current is thus used for detecting the nucleic acid molecules.

Figure 3B:
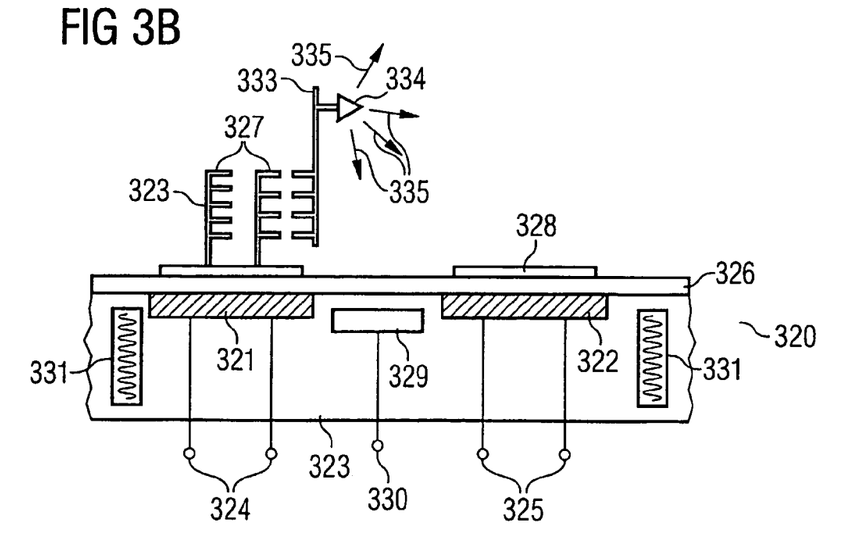

FIG. 3b shows a further biosensor 320 of the invention, which can be used to perform a further method described here.

The biosensor 320 has a first photodiode 321 and a second photodiode 322, which are introduced into an insulator layer 323 made of insulator material such as silicon. The photodiodes 321, 322 are connected to an evaluation unit (not illustrated) via first and second electrical connections 324 and 325.

The biosensor 320 furthermore has an oxide layer 326, on which the units 327 and 328 for immobilizing nucleic acids are situated. These immobilization units 327, 328 are formed from gold. As an alternative, the immobilization units 306 may also be produced from silicon oxide and may be coated with an e.g. abovementioned material which is suitable for immobilizing capture molecules.

Furthermore, the biosensor 320 has an electrode 329 with an electrical connection 330 adjacent to the units 327 and 328. An electrical potential can be applied to the electrode 329 and the hybridization and/or the denaturing process can thereby be accelerated.

Finally, a thermostatically regulating unit 331 is situated in the sensor 320.

Capture molecules 332 are immobilized on the immobilization unit 327. FIG. 3b shows the sensor in the state in which nucleic acid molecules 333 to be detected have formed double-stranded hybrid molecules with the capture molecules 332. The nucleic acid molecules 333 carry a fluorophor 334 as a marking which can emit fluorescent radiation. This radiation, indicated by the arrows 335, can be detected by the photodiode 321.

As a further exemplary embodiment of a method disclosed here, mention shall be made of the redox recycling method with the known electrode arrangement in accordance with FIG. 4. In this embodiment, after the double-stranded hybrid molecules have been formed (cf. FIG. 4c), the molecule 409 is cleaved by means of the enzyme 408 and the above-described redox recycling process is thereby initiated. As a result of an increase in temperature above the melting point of the hybrid comprising capture molecule 405 and nucleic acid 407 to be detected, the enzyme 408 bonded to the nucleic acid molecule 407 is removed from the electrode surface and so no new redox pairs which can contribute to the current flow are formed there from the molecule 409. This spontaneous change in conductivity between interdigital electrode structures, for example, is used for detecting the nucleic acids.

In a further alternative embodiment, it is possible to provide a one- or multidimensional array of detection units, and a plurality of thermostatically regulating units. A thermostatically regulating unit is respectively arranged at least below a portion of the detection units, preferably below each detection unit. Each thermostatically regulating unit can be driven and regulated individually, so that each detection unit can be locally heated.

Figure 7:
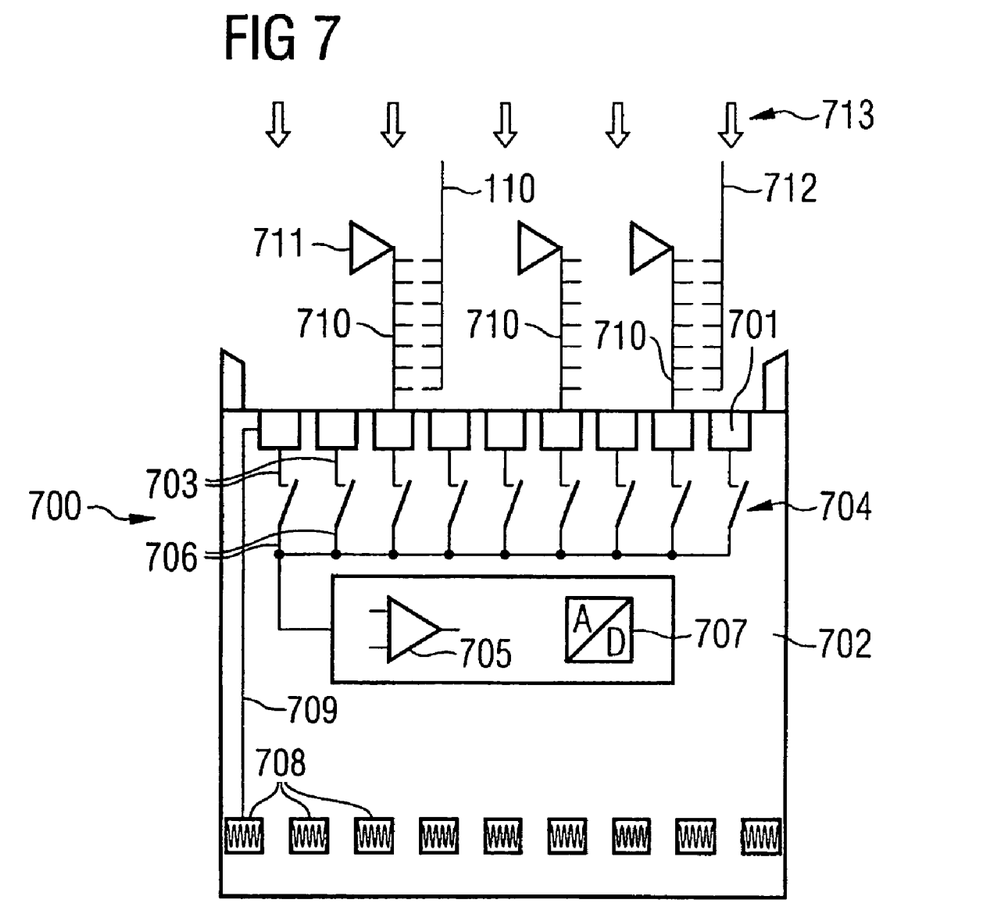
FIG. 7 shows a biosensor on the basis of which a further type of implementation of a method of the invention is illustrated.

FIG. 7 shows a biosensor 700 having immobilization units 701 arranged in an insulator layer 702 made of insulator material.

The immobilization units 701 are connected via electrical connections 703 to an electrical detection circuit 704, which are part of the detection unit of the sensor. The immobilization units 701 are produced from gold.

The electrical detection circuit 704 of the biosensor 700 has a preamplifier 705 for the amplification of the detected signal for each immobilization unit, selection electronics 706 for the individual selection of at least one immobilization unit, and also an analog/digital converter 707 for the conversion of the detected signal for each immobilization unit.

Moreover, the biosensor has thermostatically regulating units 708 which can individually drive and regulate the temperature of each of the units 701, e.g. via an electrical connection 709. For the sake of clarity, such a connection 709 is shown only for one thermostatically regulating unit 708.

Single-stranded DNA probe molecules 710 having a redox-active marking 711 are applied on the immobilization units 701. Said marking 711 may be e.g. a photosynthetic bacterial reaction center and, as described in WO 00/42217 A1 on page 50, fourth paragraph to page 52, first paragraph, be linked to the probe molecules (also cf. FIG. 6c).

In order to detect nucleic acids, the biosensor 700 is brought into contact with a sample to be examined, for instance an electrolyte (not shown).

FIG. 7 shows the biosensor 700 for the case where the electrolyte contains DNA strands 712 having a predetermined nucleotide sequence which is complementary to the sequence of the DNA probe molecules 710.

As can be seen from FIG. 7, the result is that after hybridization has been effected, hybridized molecules are situated on the units 701, i.e. double-stranded DNA molecules are immobilized there.

By means of a light source (e.g. a laser) that is not shown, light—symbolized by arrows 713—having a wavelength suitable for exciting the markings 711, such as e.g. a bacterial reaction center, is thereupon radiated in. This results in a photoinduced charge separation within the cofactors of the reaction center and in intermolecular electron transfer.

If a suitable potential is present at the immobilization units 701 (determined by the selection electronics), an electron is transferred from the double-stranded hybrid molecules to the units 701, i.e. a current flow occurs which is detected by the electrical detection circuit 704.

The temperature at the selected units 701 is then increased to a temperature above the melting point Tm by the corresponding thermostatically regulating units 708. This results in denaturing and separation into the single strands, and thus also in an interruption of the current flow, since the single-stranded molecules 710 are almost perfect insulators. This change in the current flow is detected by the circuit 704 of the detection unit on the basis of a second, preferably continuous, measurement. The presence of the DNA molecules 712 is determined by means of comparison of the two electrical measurements.

The use of the biosensor 700 described here permits not only a very sensitive, but also an individual (and spatially resolved) detection of one or more immobilization units and furthermore affords a distinct simplification of the entire measurement arrangement.

The invention claimed is:

1. A method for detecting macromolecular biopolymers, comprising the steps of:
   bringing a sample into contact with at least one unit for immobilizing macromolecular biopolymers where the at least one unit for immobilizing macromolecular biopolymers is provided with first molecules which serve as capture molecules, it being possible for the sample to contain macromolecular biopolymers, and the macromolecular biopolymers or the first molecules having a marking which is used to generate a detectable signal;

binding the macromolecular biopolymers contained in the sample to the capture molecules, thereby forming complexes comprising the capture molecules and the macromolecular biopolymers;

exciting the emission of a signal by means of the marking;

detecting the signal emitted by means of the marking;

separating the complexes, thereby essentially instantaneously changing the intensity of the emitted signal; and detecting the separation of the complexes by means of the essentially instantaneous change in the intensity of the signal, whereby the macromolecular biopolymers are detected.

2. A method for detecting macromolecular biopolymers using an electrode arrangement, comprising the steps of:

bringing a sample into contact with at least one unit for immobilizing macromolecular biopolymers where the at least one unit for immobilizing macromolecular biopolymers is provided with first molecules which serve as capture molecules, it being possible for the sample to contain macromolecular biopolymers;

binding the macromolecular biopolymers contained in the sample to the capture molecules, thereby forming complexes comprising the capture molecules and the macromolecular biopolymers;

carrying out a first electrical measurement;

separating the complexes, thereby essentially instantaneously changing the value of the electrical measurement;

carrying out a second electrical measurement out after the separation; and detecting the separation of the complexes by means of the essentially instantaneous change in the value of the electrical measurement, whereby the macromolecular biopolymers are detected.

3. The method as claimed in claim 2, wherein the step of carrying out the first and/or second electrical measurement comprises the step of measuring at the interface between the immobilization unit and the sample a potential at an electrode, the capacitance, the electrical resistance, the electrical current flow or the electrical potential.

4. The method as claimed in claim 1, further comprising the step of detecting nucleic acids, proteins or complexes comprising nucleic acids and proteins as macromolecular biopolymers.

5. The method as claimed in claim 4, wherein nucleic acid molecules are used as macromolecular biopolymers and as capture molecules so that double-stranded hybrid molecules are formed as complexes.

6. The method as claimed in claim 5, wherein the first nucleic acid molecules serving as capture molecules are single-stranded molecules.

7. The method as claimed in claim 6, wherein the separation of the hybrid molecules comprising capture molecules and nucleic acid molecules to be detected is effected by increasing the temperature to a temperature above the melting point of the double-stranded hybrid molecules.

8. The method as claimed in claim 7, wherein the temperature is controlled by a temperature regulating unit integrated into a biosensor having the at least one immobilization unit.

9. The method as claimed in claim 1, wherein the at least one immobilization unit is arranged adjacent to at least one operating electrode.

10. The method as claimed in claim 9, wherein the immobilization unit is arranged above the operating electrode.

11. The method as claimed in claim 1, wherein at least one immobilization unit is applied directly on an operating electrode or a photodiode.

12. The method as claimed in claim 1, wherein the at least one immobilization unit is configured as an operating electrode.

13. The method as claimed in claim 9, further comprising the step of applying a negative electrical potential to an operating electrode for the purpose of separating the hybrid molecules.

14. The method as claimed in claim 10, further comprising the step of applying a negative electrical potential to an operating electrode for the purpose of separating the hybrid molecules.

15. The method as claimed in claim 11, further comprising the step of applying a negative electrical potential to an operating electrode for the purpose of separating the hybrid molecules.

16. The method as claimed in claim 12, further comprising the step of applying a negative electrical potential to an operating electrode for the purpose of separating the hybrid molecules.

17. The method as claimed in claim 9, further comprising the step of applying a positive electrical potential to an operating electrode for the purpose of forming double-stranded hybrid molecules comprising capture molecules and nucleic acid molecules to be detected.

18. The method as claimed in claim 10, further comprising the step of applying a positive electrical potential to an operating electrode for the purpose of forming double-stranded hybrid molecules comprising capture molecules and nucleic acid molecules to be detected.

19. The method as claimed in claim 11, further comprising the step of applying a positive electrical potential to an operating electrode for the purpose of forming double-stranded hybrid molecules comprising capture molecules and nucleic acid molecules to be detected.

20. The method as claimed in claim 12, further comprising the step of applying a positive electrical potential to an operating electrode for the purpose of forming double-stranded hybrid molecules comprising capture molecules and nucleic acid molecules to be detected.

21. The method as claimed in claim 13, further comprising the step of applying a positive electrical potential to an operating electrode for the purpose of forming double-stranded hybrid molecules comprising capture molecules and nucleic acid molecules to be detected.

22. The method as claimed in claim 1, further comprising the step of arranging a plurality of units for immobilizing macromolecular biopolymers in an array.

23. The method as claimed in claim 1, wherein the marking is selected from a group consisting of fluorescent dyes, chemiluminescence markings, enzymes, and enzyme ligands.

24. The method as claimed in claim 22, wherein the marking is an enzyme which effects a reduction/oxidation recycling process.

* * * * *